(12) United States Patent
Fischer et al.

(10) Patent No.: US 10,822,548 B2
(45) Date of Patent: Nov. 3, 2020

(54) PROCESS FOR THE STEAM CRACKING OF ETHANE

(71) Applicant: IFP Energies nouvelles, Rueil-Malmaison (FR)

(72) Inventors: Beatrice Fischer, Lyons (FR); Vincent Coupard, Villeurbanne (FR); Mathieu Rinaudo, St Andeol Le Chateau (FR)

(73) Assignee: IFP Energies nouvelles, Rueil Malmaison (FR)

( * ) Notice: Subject to any disclaimer, the term of this patent is extended or adjusted under 35 U.S.C. 154(b) by 0 days.

(21) Appl. No.: 16/256,413

(22) Filed: Jan. 24, 2019

(65) Prior Publication Data

US 2019/0225893 A1   Jul. 25, 2019

(30) Foreign Application Priority Data

Jan. 24, 2018   (FR) ..................... 18 50558

(51) Int. Cl.
*C10G 9/36*   (2006.01)
*C10G 65/12*   (2006.01)
(Continued)

(52) U.S. Cl.
CPC .............. *C10G 9/36* (2013.01); *C07C 2/76* (2013.01); *C07C 5/327* (2013.01); *C10G 65/12* (2013.01);
(Continued)

(58) Field of Classification Search
CPC .......... C10G 9/36; C10G 11/00; C10G 65/12; C10G 69/06; C10G 2300/807;
(Continued)

(56) References Cited

U.S. PATENT DOCUMENTS

2005/0107650 A1   5/2005   Sumner
2007/0112236 A1   5/2007   Bridges
(Continued)

OTHER PUBLICATIONS

Fogler, H.S. (2016) Elements of Chemical Reaction Engineering, Prentice-Hall, 992 pgs [Office action cites section 2.5.1 "CSTRs in Series"].*

(Continued)

*Primary Examiner* — Brian A McCaig
(74) *Attorney, Agent, or Firm* — Millen White Zelano and Branigan, PC; Csaba Henter

(57) ABSTRACT

The invention relates to a process for the steam cracking of a feedstock composed of at least 80% by weight, in particular of at least 90% by weight, of ethane, the process comprising a steam cracking of the feedstock in a furnace (2), then a quenching of the pyrolysis products, then a compression operation, then a series of successive operations on the products resulting from the quenching, the said series of operations comprising a washing operation, followed by a drying operation and at least one compression operation, and finally a fractionation by cryogenic distillation. A selective hydrogenation operation, followed by a catalytic conversion operation, will be inserted into the said process, after the drying operation and before the fractionation, in order to partially convert the ethylene predominantly into propylene.

19 Claims, 4 Drawing Sheets

(51) Int. Cl.
*C10G 69/06* (2006.01)
*F25J 3/02* (2006.01)
*C07C 2/76* (2006.01)
*C07C 5/327* (2006.01)

(52) U.S. Cl.
CPC .......... *C10G 69/06* (2013.01); *F25J 3/0219* (2013.01); *F25J 3/0242* (2013.01); *C10G 2300/1081* (2013.01); *C10G 2300/807* (2013.01); *C10G 2400/20* (2013.01); *C10G 2400/30* (2013.01)

(58) Field of Classification Search
CPC ........ C10G 2300/1081; C10G 2400/20; C10G 2400/30; C07C 2/76; C07C 5/327; F25J 3/0219; F25J 3/0242
See application file for complete search history.

(56) References Cited

U.S. PATENT DOCUMENTS

| | | | |
|---|---|---|---|
| 2014/0296597 A1* | 10/2014 | Keusenkothen | C07C 5/09 585/330 |
| 2015/0232395 A1* | 8/2015 | Nyce | C07C 4/02 518/705 |

OTHER PUBLICATIONS

Harper, S.E. et al. (1999) Oil & Gas Journal, 97, 9, 49-51.*
Sanfilippo, D. et al. (2005) Sustainable Strategies for the Upgrading of Natural Gas: Fundamentals, Challenges, and Opportunities, Springer, 217-247.*
Search report in corresponding FR 1850558 dated Oct. 4, 2018 (pp. 1-2).

* cited by examiner

PROCESS FOR THE STEAM CRACKING OF ETHANE

FIELD OF THE INVENTION

The invention relates to the technology of steam cracking, which consists of the pyrolysis of saturated hydrocarbons, resulting from natural gas or from oil, in the presence of steam. Steam cracking produces, in the first place, ethylene but also propylene and, depending on the feedstock used, a $C_4$ cut rich in butadiene and a $C_5+$ (hydrocarbons having five or more carbons) cut having a high content of aromatics. Furthermore, this inventory does not take into account the light or heavy constituents which, within even the steam cracking, constitute a source of energy.

Steam cracking generally comprises a high-temperature heating operation in a furnace, followed by a quenching, by a series of operations such as washing with sodium hydroxide solution, drying or compression, before ending in a fractionation by cryogenic distillation, which is optionally combined with one or more selective hydrogenations.

PRIOR ART

Steam cracking processes suited to the type of feedstock used have already been described. This is, for example, the case of Patent FR 2 794 469, which describes a very severe steam cracking of a feedstock comprising at least 80% by weight of hydrocarbons having from 2 to 4 carbon atoms and at least 20% by weight of hydrocarbons of the ethane and propane group, with a furnace, the proportioning of the components of which was studied in order to achieve a threshold degree of conversion of ethane or propane, depending on the composition of the initial feedstock.

Many steam cracking plants were originally designed to treat feedstocks of naphtha type, naphtha denoting a petroleum cut, the lightest constituents of which have five carbon atoms and the boiling point of which can range up to 200° C. In point of fact, increasingly, these plants have to treat ethane-based feedstocks, ethane being a cheaper product and obtained from shale gas. 1.25 tonnes of ethane, instead of 3 tons of naphtha, are sufficient to produce 1 tonne of ethylene by steam cracking.

However, this change in type of feedstock is not without disadvantages, in terms of type of product obtained and in terms of impact on the plants.

This is because, in the fractionation section of the plants, the refrigerated units provided for the cryogenic distillation do not really make it possible to produce more ethylene than at the inlet of the distillation unit. The feedstock flow rate is thus lower than with naphtha and the steam cracking furnaces provided originally for naphtha are thus underused.

In addition, the lower molar mass of the products obtained, mainly ethylene, methane and hydrogen, in comparison with the products obtained from a naphtha feedstock, can present problems in the compression means: it may prove necessary to raise the pressure in the furnaces and often to substantially modify the compressors in order to arrive at the pressure desired in the fractionation section. On the other hand, the distillation columns provided for propylene and the other olefins become oversized, indeed virtually useless.

Furthermore, an ethane feedstock produces virtually exclusively ethylene and hydrogen and virtually no propylene, butenes or pyrolysis gasoline. In point of fact, it can be advantageous to also have a significant proportion of olefins/unsaturates/aromatics of at least three or of at least four carbons, as these are starting products of high enhanceable value in chemistry.

The aim set by the invention is that of providing a process for making it possible for steam cracking plants to operate better with a feedstock which is other than a feedstock of naphtha type, more particularly in order to better adapt them to a feedstock based on ethane.

The invention is more particularly targeted at increasing the amount of ethane feedstock which can be treated in a steam cracking plant.

Another aim of the invention is to obtain, by steam cracking of feedstock of ethane type, a substantial increase in the products heavier than ethylene and in particular in the products of unsaturated type with a mean molar mass greater than that of ethylene (or with a carbon number greater than that of ethylene).

SUMMARY OF THE INVENTION

The invention has first of all, as subject-matter, a process for the steam cracking of a feedstock composed of at least 80% by weight, in particular of at least 90% by weight, of ethane, the process comprising a steam cracking of the feedstock in a furnace, then a quenching of the pyrolysis products, then a compression operation, then a series of successive operations on the products resulting from the quenching, the said series of operations comprising a washing operation, followed by a drying operation and at least one compression operation, and finally a fractionation by cryogenic distillation.

According to the invention, a selective hydrogenation operation, followed by a catalytic conversion operation, is inserted into the said process, after the drying operation and before the fractionation, on the products obtained after drying, in order to partially convert the ethylene predominantly into propylene.

Preferably, according to the invention, the ethylene is partially converted into propylene and into other components of unsaturates type, such as butene, and/or of aromatics type.

The compounds obtained can also comprise, as minor constituents, coproducts in the form of saturated hydrocarbons, such as propane.

By thus supplementing the known steam cracking process by intermediate operations, a portion of the ethylene will be converted into compounds of higher molar mass, predominantly propylene but also butenes and aromatics, which constitute major starting materials for the petrochemical industry which are highly enhanceable in value.

This partial conversion of the ethylene is preferably carried out at a compression pressure intermediate between the steam cracking operating pressure (in the furnace) and the fractionation operating pressure.

It should be emphasized that, by thus increasing the mean molar mass by partial conversion of ethylene, the conversion effluent is more easily compressed: it is also possible to rebalance the cryogenic distillations during the fractionation which takes place after this catalytic conversion, and it is possible, with the same refrigeration units, to produce more olefins in total. More feedstock can thus be treated and thus better use may be made of the existing furnaces.

The additional operations thus added are thoroughly inserted into the steam cracking process, by adding units for carrying them out (described in detail later), but without having to withdraw or significantly modify the units or components already present in a plant of steam cracking type. The invention thus does not require a complete recasting of the steam cracking process and plant.

As also described in detail later, the process according to the invention offers great flexibility in its implementation. It makes it possible in particular to precisely control the ratio of the amount of olefins and of unsaturates, of aromatics having more than 3 carbon atoms obtained (predominantly propylene) to the amount of ethylene, according to requirements.

The catalytic conversion operation uses a suitable catalyst, which preferably comprises a zeolite which, at high temperature (between 500 and 650° C.), makes it possible to operate without being excessively rapidly deactivated. Any zeolite which makes it possible to carry out olefin interconversion reactions (that is to say, reactions for conversion between olefins, as is done by the conversion unit) is suitable for this process. The preferred catalyst is a catalyst comprising ZSM-5 on an inert matrix, for example silica. Post-treatments can be carried out on this catalyst in order to limit its cycle deactivation. The ratio of the hourly mass flow rate of olefins to be converted to the weight of catalyst is between 1 and 20 and preferably between 3.5 and 10.

Preferably, the catalytic conversion operation is followed by at least one compression operation, in particular having two stages, and preferably by two compression operations, before the fractionation. This is because it is useful to recompress the effluents resulting from the catalytic conversion at this step, as this conversion takes place at a relatively low pressure, and it is advantageous to reinject the gas stream into the remainder of the steam cracking line at the usual pressure necessary in order to undergo the fractionation by cryogenic distillation.

Preferably, a feedstock/effluent exchange operation is carried out on the products obtained during the catalytic conversion operation. The use of an exchanger will carry out a preheating of the gases before they are subjected to the high-temperature catalytic conversion.

According to a first alternative form, the catalytic conversion operation is carried out in several reactors in series.

According to another alternative form, it is carried out in a single reactor.

The catalytic conversion operation can thus be carried out in one reactor or in several reactors in series and, preferably, a portion of the products obtained by the catalytic conversion at the outlet of the one or the reactors is recycled by reintroducing them, after a compression operation, into the said reactor or reactors. The recycling is favoured in particular in the alternative form having just one reactor.

The degree of recycling can be adjusted and makes it possible, among other operating parameters, to regulate the degree of conversion of the ethylene to propylene and other unsaturates/aromatics at the desired degree.

The two alternative forms each exhibit advantages: —to have just one reactor is a simpler solution, which is more compact in the congested environment of a steam cracking plant, which generally requires high recycling, with a high conversion of the ethylene, —to have two or more than two reactors in series is admittedly a more complex solution to implement, taking up more room in the plant, all the more so because, as the conversion reaction is exothermic, it is necessary to provide a cooler at the outlet of each reactor, but it makes it possible to operate without recycling, in the case where a reduced conversion of ethylene is desired.

Preferably, the products obtained at the outlet of the, of at least one of the or of each of the reactors are cooled, in order to compensate for the highly exothermic nature of the catalytic conversion. This cooling is recommended in particular when there are several reactors in series (and which cannot carry out recycling or can only carry out a little recycling, in contrast to the alternative form having just one reactor).

Advantageously, it is also possible to carry out a compression operation after the quenching, in particular a three-stage compression, and before the washing operation, as in a conventional naphtha steam cracking process.

Preferably, a gas/liquid separation is carried out of the products obtained after the catalytic conversion and before a compression operation: this thus ensures that the gaseous effluents entering the compressors are devoid of traces of liquid which would interfere with the satisfactory operation thereof.

Preferably, the selective hydrogenation and the partial catalytic conversion of the ethylene are carried out at pressures intermediate between that of the steam cracking operation and that of the fractionation operation.

The intermediate pressure in the selective hydrogenation unit (at the inlet of the hydrogenation reactor) can thus be between 5 and 20 bars, i.e. between $5\times10^5$ and $2\times10^6$ Pa, preferably between 15 and 20 bars. It can also be higher than these values, a high pressure being favourable for the hydrogenation reactions.

The operating temperature of the hydrogenation is not very high, generally between 30 and 120° C., preferably between 40 and 60° C.

The intermediate pressure in the partial catalytic conversion of the ethylene is for its part preferably markedly lower. It is, for example, less than or equal to 10 bars, that is less than $10^6$ Pa. It can be of the order of 3 to 10 bars, for example of the order of 3 to 6 bars. The olefin partial pressure is, for example, from approximately 0.5 to 3 bars, preferably of between 1 and 2 bars, in particular of approximately 1.5 bars.

These intermediate pressure values, in particular in the unit for the catalytic conversion of ethylene, thus remain very generally lower than the pressures encountered at the inlet of the fractionation unit, which can, for example, be of the order of 30 to 35 bars (i.e. of the order of $3\times10^6$ to $3.5\times10^6$ Pa), which explains why the implementation of the invention may require compression means additional to those already present on the steam cracking line.

It is also possible to recycle a portion of the products obtained at the outlet of the fractionation by reintroducing them into the steam cracking furnace, in a conventional way.

Another subject-matter of the invention is a plant for the steam cracking of a feedstock composed of at least 80% by weight, in particular of at least 90% by weight, of ethane, making it possible to implement the abovementioned process.

Such a plant comprises, in series: —a steam cracking furnace, —a quenching unit, —a first compression means, then a series of units comprising a washing unit, a drying unit and at least one second compression means, then—a unit for fractionation by cryogenic distillation.

"Compression means" is understood to mean, within the meaning of the invention and throughout the present text, one or more compressors in series, optionally with: —coolers between each compressor, when there are several of them, and—means for separating the liquid before the compressors.

According to the invention, it also comprises, between the drying unit and the fractionation unit, a selective hydrogenation unit, followed by a catalytic conversion unit (for catalytic conversion on the products obtained after drying) in order to partially convert the ethylene predominantly into propylene.

Preferably, according to the invention and as seen above, with the plant, the ethylene is partially converted into propylene and into other components of unsaturates type, such as butene, and/or of aromatics type, it being possible for the compounds obtained to also comprise, in a minor fashion, coproducts in the form of saturated hydrocarbons, such as propane.

Preferably, the catalytic conversion unit comprises one or more compression means, in particular two-stage compression means.

The conversion unit according to the invention preferably comprises a feedstock/effluent heat exchanger. This exchanger makes it possible to heat the feedstock up to the operating temperature, by virtue of the high exothermicity of the reaction in the reactor or reactors of the unit. The expression "feedstock/effluent" relating to the exchanger is conventional for an exchanger; the "feedstock" in this instance is not the initial feedstock which will feed the steam cracking furnace but the products obtained subsequent to the different operations undergone by the feedstock feeding the said furnace and which enter the exchanger in question.

The catalytic conversion unit comprises one reactor or several reactors in series: as indicated above, the two alternative forms have their advantages. The reactor or reactors used for the $C_2--$ into $C_3--$conversion reaction are preferably reactors of radial type, that is to say having transverse flow of the feedstock through the catalytic bed. The catalytic bed can be of the fixed bed or moving bed type. A moving bed is a gravity flow bed for the catalytic solid used of the type of that which is encountered in units for the catalytic reforming of petroleums. The operating temperature in the catalytic conversion reactor or reactors is preferably between 500 and 650° C., in particular at least 550° C. within this interval.

Preferably, cooling means are positioned at the outlet of the or of each of the reactors. They are provided in particular at the outlet of each of the reactors in the alternative form where several reactors are used in series (with no or little recycling).

A compression means is preferably positioned between the quenching unit and the washing unit, in a conventional way in steam cracking plants.

One or more compression means are also advantageously positioned between the catalytic conversion unit and the unit for fractionation by cryogenic distillation, in order to increase the pressure of the gaseous effluents in order for the remainder of the operations, in particular the fractionation, to be able to be carried out conventionally at the appropriate pressure, the passage into the hydrogenation unit and the catalytic conversion unit naturally bringing about a decrease in the pressure.

The catalytic conversion unit thus comprises one reactor or several reactors in series. In particular in the case with just one reactor, it is possible to provide recycling means at the outlet of this reactor for reintroduction of a portion of the products into the reactor or reactors after compression. This recycling makes it possible to increase the degree of conversion of the ethylene and to reduce the increase in temperature due to the reaction, which can make it possible, with a sufficient amount of recycling, to operate with just one reactor.

It is also possible to provide a gas/liquid separation means, of the demisting vessel type, positioned at the outlet of the catalytic conversion unit, in order to protect the compression means positioned downstream, as seen above.

The plant is preferably also provided with means for recycling a portion of the products obtained at the outlet of the fractionation unit for reintroduction into the steam cracking furnace, in a conventional way.

Another subject-matter of the invention is the use of the process or of the plant which are described above for carrying out the steam cracking of a feedstock composed of at least 80% by weight, in particular of at least 90% by weight, of ethane, in order to increase the content of at least one compound chosen from propylene, butenes, aromatics and petrol of the products obtained, and very particularly preferably propylene. Advantageously, propylene is predominantly concerned.

BRIEF DESCRIPTION OF THE DRAWINGS

The invention will be described in more detail below using nonlimiting examples of the process according to the invention, illustrated by the following figures.

The same references correspond to the same components in all the figures. Generally, throughout the present text, when it is mentioned that a section/operation is "followed" by another, or when the terms of "upstream" or "downstream" type are mentioned, reference is made to the general direction of progress of the feedstock from its entry into the steam cracking furnace up to its departure from the unit for fractionation by distillation.

Figure 1:
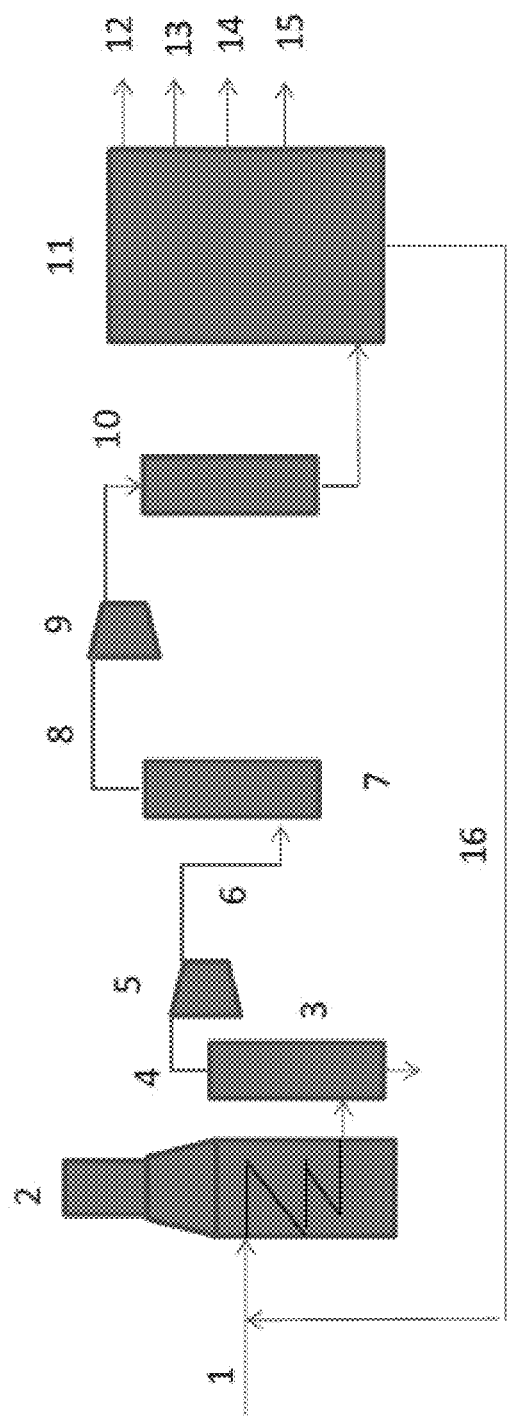
FIG. 1: a block diagram representation of a steam cracking plant provided for treating naphtha in a conventional way.

Description of FIG. 1

The feedstock arrives via the pipe 1 as a mixture with steam towards the steam cracking furnace 2. At the outlet of the furnace, the effluent is conveyed to a quenching section 3 producing a rapid quenching of the effluent and a first fractionation, which will remove the heaviest fractions and the condensed water. The gaseous fraction exiting from this section is conveyed via the pipe 4 to a compression section 5, generally comprising three compression stages and intermediate condensations. On departing from this section 5, the gaseous fraction is conveyed via the pipe 6 to a section for washing with sodium hydroxide solution 7. The gaseous outflow from this washing operation is conveyed via the pipe 8 to a further compression section 9. At the outlet of the compression 9, the compressed gas is conveyed to a drying section 10 and then to a section 11 for cryogenic distillation and for selective hydrogenations. This section makes it possible to fractionate the gas: there is a hydrogen outlet 12, a combustible gas outlet 13, an ethylene outlet 14 and a $C_3+$ outlet 15 ($C_3+$ are the hydrocarbons comprising at least three carbons: propylene and heavier than propylene). The ethane outlet 16 makes it possible to recycle the unconverted ethane to the steam cracking furnace 2.

Figure 2:
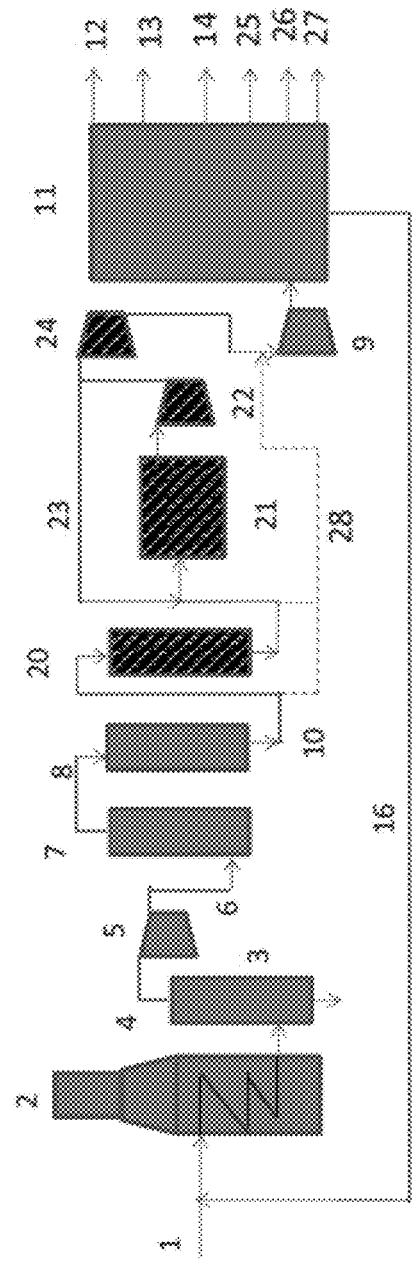
FIG. 2: the plant of FIG. 1 modified according to the invention in order to be suitable for a feedstock of ethane type by incorporating an ethylene conversion unit.

Description of FIG. 2

The feedstock arrives via the pipe 1 as a mixture with steam towards the steam cracking furnace 2. At the outlet of the furnace, the effluent is conveyed to a quenching section 3 producing a rapid quenching of the effluent and a first fractionation, which will remove the heaviest fractions and the condensed water, and the gaseous fraction exiting from this section is conveyed via the pipe 4 to a compression section 5, generally comprising three compression stages and intermediate condensations. At the outlet of this section 5, the gaseous fraction is conveyed via the pipe 6 to a section for washing with sodium hydroxide solution 7. The gaseous outflow from this washing operation is conveyed via the pipe 8 to a drying section 10.

At the outlet of the drying 10, the gas is subjected to a selective hydrogenation section 20 which removes all the diolefins which, at high temperature, might foul the items of equipment of the conversion section 21 which is positioned following the selective hydrogenation section 20. In this section 21, approximately 30% of the ethylene is converted per pass to produce mainly propylene but also butenes and aromatics. This section 21 is at a fairly low pressure, of at most 20 bars; it is thus necessary to recompress the stream at the outlet. This recompression takes place in two stages; a first stage with the compression section 22 makes it possible to achieve a pressure sufficient to recycle a portion 23 of the effluent towards the conversion section 21, so as to increase the ethylene conversion; the remainder is recompressed by the compression section 24. It is then directed into the final existing compression section 9 (already present in the conventional steam cracking line of FIG. 1) and then towards the fractionation section 11. The items of equipment for the fractionation of the $C_3+$ compounds already exist in a steam cracking plant originally designed for naphtha: they thus make possible the departure from this section, apart from the hydrogen 12, the combustible gas 13 and the ethylene 14, of propylene 25, butenes 26 and petrol 27. The ethane outlet 16 makes it possible to recycle the unconverted ethane to the steam cracking furnace 2. A bypass line 28 connecting the outlet of 10 or 20 to the inlet of the compression section 9 makes it possible to operate with a variable and flexible feedstock in the section according to the invention (it is optional).

Figure 3:
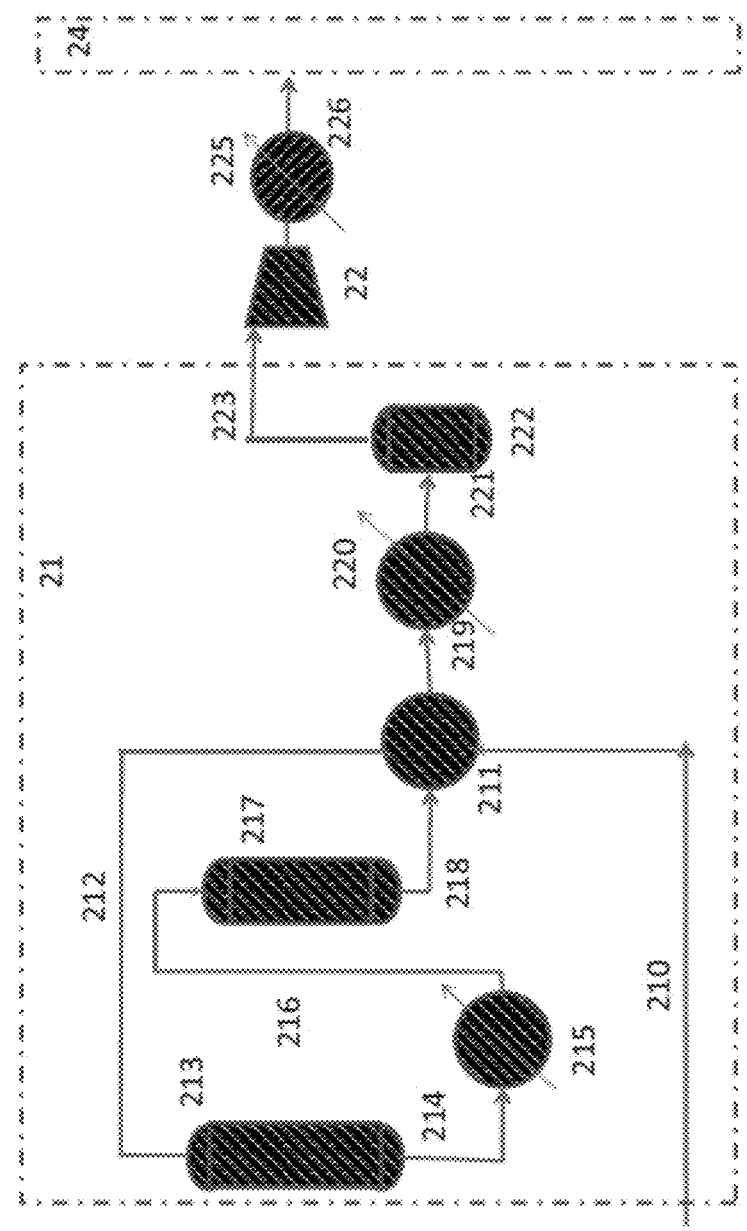
FIG. 3: a detailed representation of a first alternative form of the ethylene conversion unit represented in FIG. 2, FIG. 4: a detailed representation of a second alternative form of the ethylene conversion unit represented in FIG. 2.

Description of FIG. 3

This figure describes in detail a first alternative form of the ethylene conversion unit 21 of FIG. 2, an alternative form comprising two (or more) reactors with intermediate cooling. The other items of equipment of the plant of FIG. 2, in particular those described as "initiation" (that is to say, the steam cracking furnace 2), and those described as "regeneration" (compressor, exchangers, separator, and the like), are not represented in FIG. 3 (or in FIG. 4).

The gas coming from the selective hydrogenation section 20 arrives via the pipe 210 at the feedstock/effluent exchanger 211, where it is preheated up to the operating temperature and conveyed via the pipe 212 to the first reactor 213. In this reactor, a zeolite-based catalyst makes it possible to convert the ethylene into propylene and other products which are enhanceable in value. As the reaction is very exothermic, it is necessary to cool the stream at the outlet of this first reactor by generation of steam 215 in order to cool the effluent 214 down to the operating temperature. The cooled stream is conveyed via the pipe 216 to the second reactor 217.

Two reactors are represented. In some cases, it may be necessary to install more of them if the concentration of ethylene at the inlet, and thus the exothermicity, is very high.

At the outlet of the reactor 217, the converted effluent is conveyed via the pipe 218 to the feedstock/effluent exchanger 211, where it is cooled by indirect exchange with the feedstock (in this instance, the products entering the exchanger in question), and then to a refrigerating means 220, where the cooling is terminated using cooling water. It is also possible to use air to provide the cooling at the refrigerating means 220. It is thus possible to use, in order to carry out this cooling, either a water exchanger or an air exchanger.

At the outlet of the heat exchanger 220, the effluent is conveyed via the pipe 221 to a demisting vessel 222, where possible traces of liquid are separated from the gas phase. The gas phase is taken up into the pipe 223, compressed by the compressor 22, cooled by the water refrigerating means 225 and then conveyed towards another compression section 24 via the pipe 226.

According to the desired degree of conversion of ethylene, a portion of the gas at the outlet of the refrigerating means/heat exchanger 225 can be recycled to the feedstock/ effluent exchanger 211. This is because the conversion of the ethylene per pass is approximately 30%; it may be necessary to have a higher conversion in order to use yet again the steam cracking furnaces.

Figure 4:
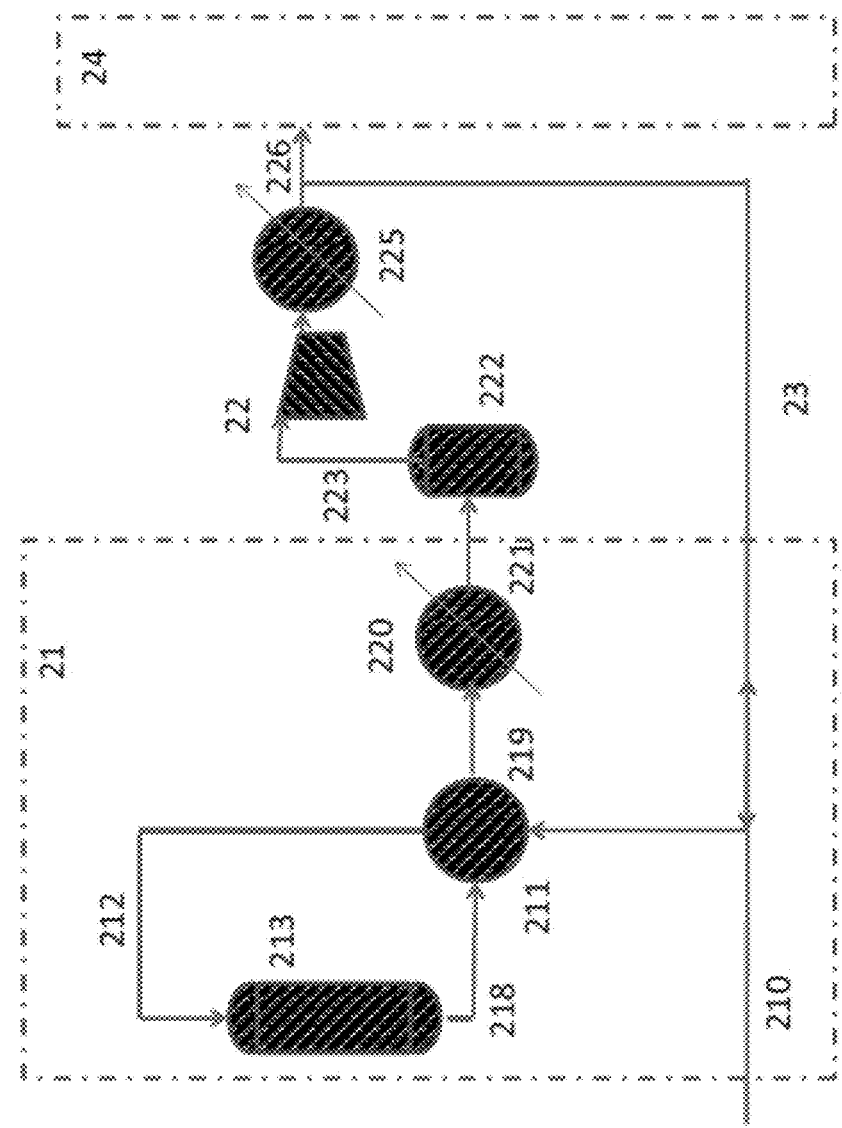

Description of FIG. 4

In this figure, according to another alternative form, the ethylene conversion unit only has a single reactor and resorts to high recycling.

The gas coming from the selective hydrogenation section 20 arrives via the pipe 210, as a mixture with the recycling gas arriving via the pipe 23, at the feedstock/effluent exchanger 211, where it is preheated up to the operating temperature and conveyed via the pipe 212 to the reactor 213. The reaction is very exothermic but, with the dilution due to high recycling, it is possible to have a moderate increase in temperature (between 30° C. and 50° C.) and thus to operate with just one reactor.

At the outlet of the reactor 213, the converted effluent is conveyed via the pipe 218 to the feedstock/effluent exchanger 211, where it is cooled by indirect exchange with the feedstock, and then to the refrigerating means 220, which is a water exchanger, where the cooling is terminated using cooling water. It is also possible to use an air exchanger. At the outlet of this exchanger, the effluent is conveyed via the pipe 221 to a demisting vessel 222, where possible traces of liquid are separated from the gas phase.

The gas phase is taken up into the pipe 223, compressed by the compressor 22, cooled by the water refrigerating means 225 and then conveyed towards another compression section 24 via the pipe 226. A portion of the compressed gas is returned, via the pipe 23, to the feedstock/effluent exchanger 211. High recycling (between 100% and 250% by weight, with respect to the feedstock) makes it possible to have just one reactor and a high conversion of the ethylene to give propylene and other advantageous compounds.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding French application No. 18/50.558, filed Jan. 24, 2018, are incorporated by reference herein.

EXAMPLES

These examples result from simulation studies. For the sake of simplification, they were worked out while regarding the feedstock as 100% ethane, whereas, under real conditions, the feedstock also contains a few percent of other compounds (less than 10% and generally at most 5% of minor compounds).

Comparative Example 1

In a first step, a base case is simulated with a naphtha steam cracker operating with an ethane feedstock, with a plant in accordance with FIG. 1.

The initial ethane feedstock comes from a series of distillations incorporating a demethanizer, which separates the methane at the top, and then a de-ethanizer, which separates the $C_3+$ compounds at the bottom. The purity is greater or lesser depending on the strictness of these distillations: in this instance, the composition of the feedstock is 96% by weight ethane, the remainder consisting of methane and propane.

The steam cracking furnace 2 treats 100 t/h of ethane, including 38 t/h of recycling and 62 t/h of fresh feedstock. The flow rate is limited by the refrigeration compressors of the fractionation section 11.

48.85 tonne/h of ethylene and 2.6 t/h of pure hydrogen are produced at the outlet of the fractionation section 11, but very few other economically enhanceable compounds.

The refrigeration compressors have a power of 2.05 MW for the ethylene compressor and of 28.9 MW for the propylene compressor.

Example 2 According to the Invention

The introduction of an ethylene conversion unit into the steam cracking installation, as represented in FIGS. 2 and 4, that is to say in the alternative form of the invention where just one catalytic conversion reactor is used, is simulated. The feedstock flow rate is increased, while keeping the power of the refrigeration compressors of the fractionation section lower than that of the base case according to Comparative Example 1.

It is then possible to treat 135.5 t/h of ethane in the steam cracking furnace, including 83 t/h of fresh feedstock and 52.5 t/h of recycling.

At the inlet of the conversion section 210, diolefins have already been hydrogenated, the pressure is 5.7 bars and the temperature is 35° C., the flow rate is 135.5 t/h, the average molar mass of the gaseous effluent is 20.1 g/mol and the molar composition is as follows (in %):

| | |
|---|---|
| Hydrogen | 32.1 |
| Methane | 4.6 |
| Ethane | 25.5 |
| Ethylene | 35.7 |
| Propane | 0.3 |
| Propylene | 0.6 |
| Butenes | 0.6 |
| $C_5+$ | 0.2 |
| CO | 0.4 |

A high recycling 23, of 240 t/h, is applied and, at the outlet 226 of the conversion section, after the cooler 225, the situation has returned to 5.7 bars and 35° C., with a flow rate still of 135.5 t/h. The average molar mass is increased to 21.9 g/mol and the molar composition is then (in %):

| | |
|---|---|
| Hydrogen | 35.0 |
| Methane | 5.0 |
| Ethane | 28.2 |
| Ethylene | 13.3 |
| Propane | 0.8 |
| Propylene | 15.4 |
| Butenes | 1.6 |
| $C_5+$ | 0.4 |
| CO | 0.4 |

At the outlet of the cryogenic fractionation section 11, 22.7 t/h of ethylene, 40.3 t/h of propylene, 3.6 t/h of pure hydrogen and 7.8 t/h of $C_4+$ are produced.

$C_4+$ and $C_5+$ represent, with the same convention as for $C_3+$, hydrocarbons respectively exhibiting at least 4 and at least 5 carbons.

The regeneration compressors have a power of 1.15 MW for the ethylene compressor and of 26.8 MW for the propylene compressor.

It is seen that, with the same refrigeration compressors, it is possible to increase the flow rate of fresh feedstock by more than 30% and to produce an amount of olefins increased by approximately 30%, while taking into account only the ethylene and the propylene. There are also other economically enhanceable products, such as butenes and aromatics.

In this scenario, there is much more propylene than ethylene: the ratio by weight is approximately 1.8.

Example 3 According to the Invention

The introduction of an ethylene conversion into the steam cracking installation, represented in FIGS. 2 and 3, that is to say in the alternative form of the invention where two catalytic conversion reactors are used in series, is simulated.

The same base case is used as in Comparative Example 1, with a naphtha steam cracker operating on ethane.

The steam cracking furnaces treat 100 t/h of ethane, including 38 t/h of recycling and 62 t/h of fresh feedstock. The flow rate is limited by the refrigeration compressors of the fractionation section. 48.85 tonne/h of ethylene and 2.6 t/h of pure hydrogen are produced, but very few other economically enhanceable compounds. The refrigeration compressors have a power of 2.05 MW for the ethylene compressor and of 28.9 MW for the propylene compressor.

The introduction of an ethylene conversion into the steam cracker, as represented in FIGS. 2 and 3, is simulated and the flow rate of feedstock is increased, while keeping the power of the refrigeration compressors of the fractionation section lower than that of the base case.

It is then possible to treat 128.1 t/h of ethane in the steam cracking furnaces, including 78.9 t/h of fresh feedstock and 49.2 t/h of recycling.

At the inlet of the conversion section 210, diolefins have already been hydrogenated, the pressure is 5.2 bars and the temperature is 35° C., the flow rate is 128.1 t/h, the average molar mass is 20.1 g/mol and the molar composition is as follows (%) (same composition as in Example 1):

| | |
|---|---|
| Hydrogen | 32.1 |
| Methane | 4.6 |
| Ethane | 25.5 |
| Ethylene | 35.7 |
| Propane | 0.3 |
| Propylene | 0.6 |

-continued

|         |     |
|---------|-----|
| Butenes | 0.6 |
| $C_5+$  | 0.2 |
| CO      | 0.4 |

The pressure is slightly lower than in Example 1 as, without recycling, the pressure at the inlet of the first conversion reactor is lower (it is adjusted in order to have 1.5 bars of olefin partial pressure).

At the outlet 226 of the conversion unit 21, after the compressor 22 and the cooler 225, the situation has returned to a pressure of 5.2 bars and to a temperature of 35° C., the flow rate is 128.1 t/h, the average molar mass has increased to 21.2 g/mol and the molar composition is then:

|           |      |
|-----------|------|
| Hydrogen  | 34.0 |
| Methane   | 4.8  |
| Ethane    | 27.2 |
| Ethylene  | 22.2 |
| Propane   | 0.4  |
| Propylene | 8.7  |
| Butenes   | 2.1  |
| $C_5+$    | 0.2  |
| CO        | 0.4  |

At the fractionation outlet, 36.9 t/h of ethylene, 22.2 t/h of propylene, 3.4 t/h of pure hydrogen and 8.6 t/h of $C_4+$ are produced.

The regeneration compressors have a power of 1.52 MW for the ethylene compressor and of 28.9 MW for the propylene compressor.

It is seen that, with the same refrigeration compressors as those used in the plant provided for treating naphtha, it is possible, in this case and without recycling, to increase the flow rate of fresh feedstock by 27% and to produce an amount of olefins increased by 21%, while taking into account only the ethylene and the propylene, as there are also other economically enhanceable products, such as butenes and aromatics.

In this case, there is less propylene than ethylene and the ratio by weight is approximately 0.6, and an even lower ratio is possible by conveying only a fraction from the outlet of the selective hydrogenation unit 20 to the conversion unit 21, which makes it possible to have the ethylene conversion below a certain threshold, for example below 30%.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A process for steam cracking of a feedstock comprising at least 80% by weight of ethane, the process comprising a steam cracking of the feedstock in a furnace (2), then a quenching of pyrolysis products, then a compression operation, then a series of successive operations on the compressed pyrolysis products resulting from the quenching and compression, wherein the series of operations comprise a washing operation, followed by a drying operation and at least one compression operation, and finally a fractionation by cryogenic distillation, wherein a selective hydrogenation operation, followed by a catalytic conversion operation with a recycle loop, is inserted into the process, after the drying operation and before the fractionation, on the products obtained after drying, in order to partially convert the ethylene predominantly into propylene.

2. The process according to claim 1, wherein the ethylene is partially converted into propylene and into other components comprising butene and aromatics.

3. The process according to claim 1, wherein the catalytic conversion operation is followed by at least one compression operation.

4. The process according to claim 1, wherein the catalytic conversion operation is carried out in one reactor (213) or in several reactors in series (213, 217).

5. The process according to claim 1, wherein the catalytic conversion operation is carried out in several reactors in series (213, 217) and is followed by a cooling operation after at least one or each of the said reactors.

6. The process according to claim 1, wherein the catalytic conversion operation is carried out in a reactor (213), wherein a portion of the products obtained by the catalytic conversion is recycled at the outlet of the reactor by reintroducing them, after a compression operation, into the reactor.

7. The process according to claim 1, wherein the selective hydrogenation and the partial catalytic conversion of the ethylene are carried out at pressures intermediate between that of the steam cracking operation and that of the fractionation.

8. The process according to claim 7, wherein the intermediate pressure during the selective hydrogenation operation is between $5\times10^5$ and $2\times10^6$ Pa.

9. The process according to claim 7, wherein the intermediate pressure during the operation of the catalytic conversion is less than or equal to $10^6$ Pa.

10. The process according to claim 1, wherein the feedstock comprises at least 90% by weight of ethane.

11. The process according to claim 1, wherein the catalytic conversion operation is followed by at least two compression operations.

12. The process according to claim 1, further comprising bypassing part of the products obtained after drying or after the selective hydrogenation to said at least one compression operation.

13. The process according to claim 1, wherein the partially converting the ethylene predominantly into propylene leads to more propylene than ethylene being present.

14. A plant for the steam cracking of a feedstock comprising at least 80% by weight of ethane, which plant is for the implementation of the process according to claim 1, the plant comprising, in series:
- a steam cracking furnace (2) to produce an effluent,
- a quenching unit (3) which quenches the effluent and conducts a first fractionation,
- a first compressor (5),
- then a series of units comprising a washing unit (7), wherein the effluent is contacted with sodium hydroxide,
- a dryer (10),
- at least one second compressor (9), and
- a unit for fractionation by cryogenic distillation (11) and comprising, between the drying unit (10) and the fractionation unit (11): a selective hydrogenation unit (20), followed by a catalytic conversion unit (21) in order to partially convert the ethylene into hydrocarbons comprising predominantly propylene, wherein the catalytic conversion unit (21) comprises a reactor (213) and a recycling pipe (23) at the outlet of the reactor for reintroduction of a portion of the product into the reactor or reactors after compression.

15. The plant according to claim 14, wherein the catalytic conversion unit (21) comprises a compressor (22, 24).

16. The plant according to claim 14, wherein the catalytic conversion unit (21) comprises one reactor or several reactors in series (213, 217).

17. The plant according to claim 16, wherein a cooler is positioned at the outlet of the reactor (213) or at the outlet of each of the reactors (213, 217).

18. The plant according to claim 14, wherein the catalytic conversion unit (21) comprises two-stage compressors.

19. The plant according to claim 14, further comprising a bypass line 28, which connects the outlet of the drying unit 10 or the outlet of the selective hydrogenation section 20 to the inlet of the at least one second compressor 9.

* * * * *